(12) United States Patent
Deller et al.

(10) Patent No.: US 6,663,851 B1
(45) Date of Patent: Dec. 16, 2003

(54) SURFACE-MODIFIED TITANIUM DIOXIDE

(75) Inventors: Klaus Deller, Hainburg (DE); Dieter Kerner, Hanau (DE); Juergen Meyer, Stockstadt/Main (DE)

(73) Assignee: Degussa AG, Duesseldorf (DE)

( * ) Notice: Subject to any disclaimer, the term of this patent is extended or adjusted under 35 U.S.C. 154(b) by 48 days.

(21) Appl. No.: 09/606,202

(22) Filed: Jun. 29, 2000

(30) Foreign Application Priority Data

Jun. 29, 1999 (DE) .......................... 199 29 845

(51) Int. Cl.[7] .............. A61K 7/42; A61K 7/00; A61K 9/16; C09C 1/36
(52) U.S. Cl. .............. 424/59; 424/60; 424/400; 424/401; 424/490; 106/436; 106/437; 106/447; 106/448; 106/820
(58) Field of Search ............... 106/436, 437, 106/447, 448, 311, 820; 424/490, 400, 401, 59

(56) References Cited

U.S. PATENT DOCUMENTS

| 4,902,570 A | 2/1990 | Heinemann et al. | | |
|---|---|---|---|---|
| 5,415,936 A | 5/1995 | Deusser et al. | | |
| 5,543,173 A | 8/1996 | Horn, Jr. et al. | | |
| 5,885,341 A | 3/1999 | Standke et al. | | |
| 5,959,005 A | 9/1999 | Hartmann et al. | | |
| 6,022,404 A | * | 2/2000 | Ettlinger et al. | 106/404 |
| 6,113,815 A | * | 9/2000 | Elfersy et al. | 252/588 |

FOREIGN PATENT DOCUMENTS

| CA | 2 205 789 | 11/1998 |
|---|---|---|
| DE | 37 07 226 | 9/1988 |
| DE | 195 00 674 | 1/1995 |
| DE | 196 39 782 | 9/1996 |
| EP | 0 808 880 | 11/1997 |
| GB | 2 296 915 | 7/1996 |
| WO | WO 98/53004 | 11/1998 |
| WO | WO 00/31178 | 6/2000 |

* cited by examiner

*Primary Examiner*—Shelley A. Dodson
(74) *Attorney, Agent, or Firm*—Oblon, Spivak, McClelland, Maier & Neustadt, P.C.

(57) ABSTRACT

A product obtained by treating surface-modified, pyrogenically produced titanium dioxide with at least one ammonium-functional silane, such as by spraying the pyrogenically produced titanium dioxide with the at least one silane, alone or in ethanol solution, and tempering, and useful in the field of cosmetics in sunblocks, in toner powders, in paints and varnishes, in silicone rubber, as abrasives and polishes, for example, in the field of CMP.

22 Claims, 1 Drawing Sheet

UV Transmission of highly-disperse titanium dioxide

- VT 1663 (Example 2)
- VT 1666 (Example 5)
- T 805, UB 453501

3% in IPP with 7% - 10% Aerosil 200
Film thickness 10 μm

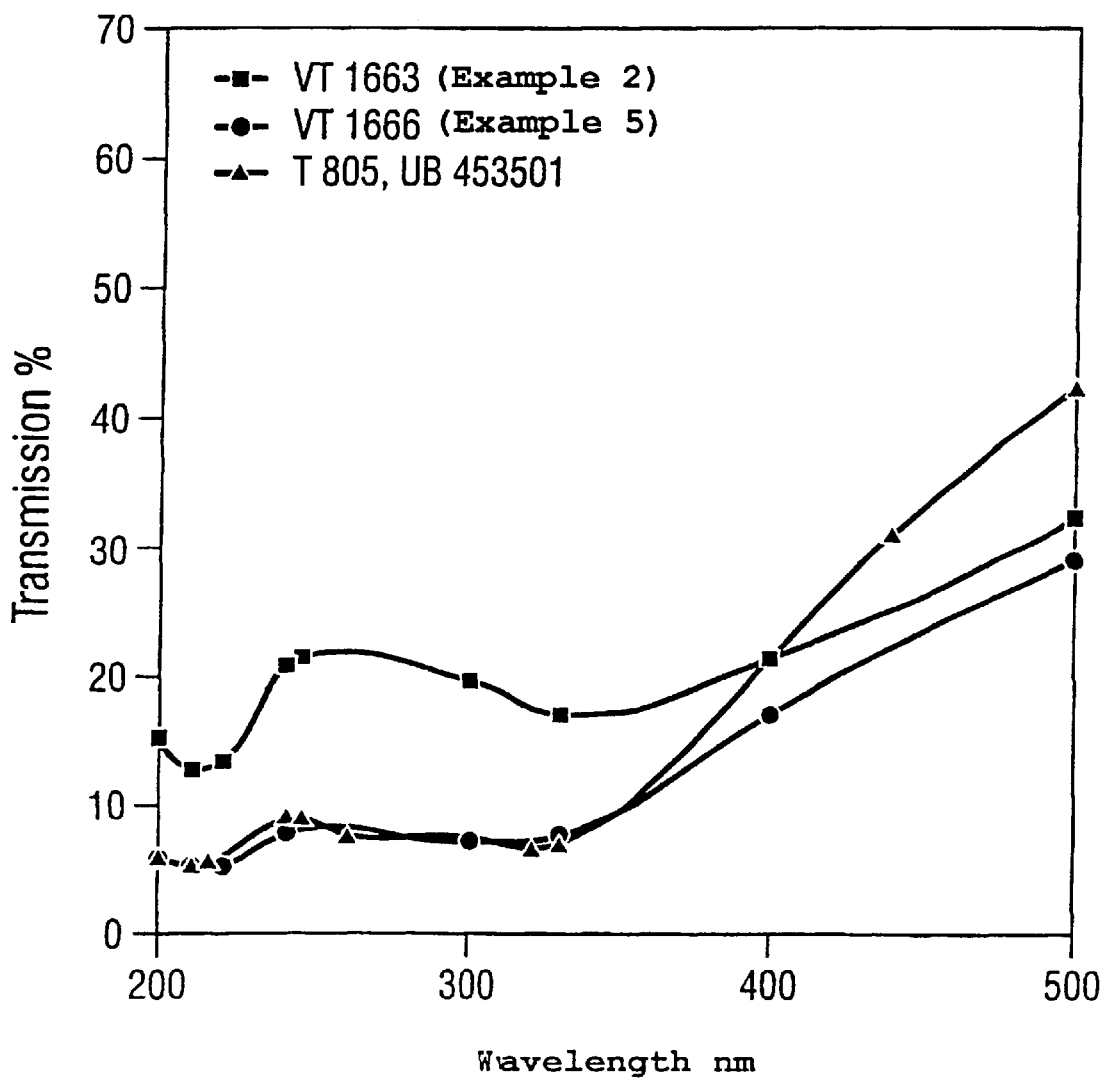

SURFACE-MODIFIED TITANIUM DIOXIDE

BACKGROUND OF THE INVENTION

1. Field of the Invention

The invention relates to a surface-modified, pyrogenically produced titanium dioxide, a process for its production as well as its use.

2. Description of the Background

It is known that highly-disperse pyrogenic titanium dioxide (for example, titanium dioxide P 25 S from Degussa-Hüls AG), on account of its low average primary particle size (21 nm) and of the structure of the aggregates and agglomerates resulting from the pyrogenic production process, has advantageous properties as a UV-A and UV-B blocker in cosmetic sunblock preparations. In addition, it is known that an increasing degree of dispersion of the titanium dioxide has a favourable effect on the UV-blocking action.

The hydrophilic surface of the pyrogenically produced titanium dioxide necessitates the use of high shear forces in order to achieve a high degree of dispersion, above all in oleophilic preparations. Consequently, pyrogenically produced titanium dioxides already surface-modified with alkylsilyl groups are known (titanium dioxide T 805 from Degussa-Hüls Aktiengesellschaft) which, in addition to the improved dispersibility in oleophilic preparations even at low shear energies, also bring about an improved UV-blocking and a decreased photochemical activity in the pyrogenic titanium dioxide. (Technical Information TI 1176 "Highly dispersed Titanium Dioxide for sunblock preparations").

A disadvantage of the known surface-modified pyrogenic titanium dioxides is the low interaction with hydrophilic constituents of the cosmetic sunblock preparations, which is due to the exclusively oleophilic character of the surface.

The object of the invention is the development of a pyrogenically produced titanium dioxide, the surface modification of which imparts to it an oleophilic as well as a hydrophilic character, and which exhibits a good dispersibility in hydrophilic and in oleophilic media.

SUMMARY OF THE INVENTION

The invention provides surface-modified, pyrogenically produced titanium dioxide, which is characterized in that it is treated with at least one ammonium-functional silane.

BRIEF DESCRIPTION OF THE DRAWINGS

FIG. 1 shows UV transmission of highly disperse titanium oxide as a function of wavelength for two examples of the present invention and a comparative material.

DETAILED DESCRIPTION OF THE INVENTION

In one embodiment of the invention, the invention is a pyrogenically produced titanium dioxide surface-modified with an ammonium-functional silane and having the following physicochemical data:

| | |
|---|---|
| BET surface area: | 15 to 100 m$^2$/g |
| Bulk density: | 150 to 700 g/l |
| pH value: | 2.5 to 8.5 |
| Loss on drying: | 0.1 to 2.0 wt. % |
| Loss on ignition: | 0.3 to 13.0 wt. % |
| Carbon content: | 0.3 to 12.0 wt. % |
| Methanol wettability: | 0 to 50 wt. % |

Another embodiment of the invention is a pyrogenically produced titanium dioxide surface-modified with:
an ammonium-functional silane corresponding to the general formula $$(RO)_{4-n+m}SiR^1_n\{(CH_2)_y(NR^2R^3R^4)^+X^-\}_m$$

n=0–3; m=1–3 with n+m<4; y=1–5; X=F, Cl, Br, or I
R=alkyl (C1–C5); R$^1$=alkyl (C1–C1 8), aryl; R$^2$ and R$^3$ independently=H, alkyl, aryl, or benzyl;
R$^4$ =H, alkyl, aryl, or —C$_2$H$_4$NR$^5$$_2$ with R$^5$=alkyl; or an ammonium-functional silane listed below:
(RO)$_3$SiC$_3$H$_6$(N$_4$C$_6$H$_{12}$)$^+$X$^-$
R=alkyl (C1–C5); X=Cl, Br, or I
(RO)$_3$SiC$_3$H$_6$(pyridinyl)$^+$X$^-$
R=alkyl (C1–C5); X=Cl, Br, or I
(RO)$_3$SiC$_3$H$_6$OCH$_2$CH(OH)CH$_2$N$^+$(CH$_3$)$_3$ X$^-$
R=alkyl (C1–l-C5); X=Cl, Br, or I; or
an ammonium-functional silane listed below:

| | |
|---|---|
| 2 Cl$^-$ | C$_6$H$_{12}$N$_4$$^{2+}$(—C$_3$H$_6$—Si(OC$_2$H$_5$)$_3$)$_2$ |
| 3 Cl$^-$ | C$_6$H$_{12}$N$_4$$^{3+}$(—C$_3$H$_6$—Si(OC$_2$H$_5$)$_3$)$_3$ |
| Cl | (CH$_3$)$_2$N—C$_2$H$_4$—N$^+$—(CH$_3$)$_2$ C$_3$H$_6$—Si(OC$_2$H$_5$)$_3$ |
| 2 Br$^-$ | CH$_2$(—$^+$N(CH$_3$)$_2$—C$_3$H$_6$—Si(OC$_2$H$_5$)$_3$)$_2$ |
| 2 I$^-$ | (—CH$_2$$^+$NH(CH$_3$)—C$_3$H$_6$—Si(OC$_2$H$_5$)$_3$)$_2$. |

Examples of ammonium-functional silanes which can be used are:
X$^-$(CH$_3$)$_3$N$^+$—C$_3$H$_6$—Si(OC$_2$H$_5$)$_3$ wherein X=Cl, Br, or I
X$^-$(C$_{18}$H$_{37}$)(CH$_3$)$_2$N$^+$—C$_3$H$_6$—Si(OC$_2$H$_5$)$_3$ wherein X=Cl, Br, or I

| | |
|---|---|
| Cl$^-$ | (CH$_3$)$_3$$^+$N—C$_3$H$_6$—Si(OC$_2$H$_5$)$_3$ |
| I$^-$ | (C$_6$H$_5$)(CH$_3$)$_2$$^+$N—C$_3$H$_6$—Si(OC$_2$H$_5$)$_3$ |
| Br$^-$ | (C$_6$H$_5$—CH$_2$)(CH$_3$)$_2$$^+$N—C$_3$H$_6$—Si(OC$_2$H$_5$)$_3$ |
| Cl$^-$ | (C$_{12}$H$_{25}$)(CH$_3$)$_2$$^+$N—C$_3$H$_6$—Si(OC$_2$H$_5$)$_3$ |
| Br$^-$ | (C$_{12}$H$_{25}$)(CH$_3$)$_2$$^+$N—C$_3$H$_6$—Si(OC$_2$H$_5$)$_3$ |
| I$^-$ | (C$_{12}$H$_{25}$)(CH$_3$)$_2$$^+$N—C$_3$H$_6$—Si(OC$_2$H$_5$)$_3$ |
| Cl$^-$ | (C$_{16}$H$_{33}$)(CH$_3$)$_2$$^+$N—C$_3$H$_6$—Si(OC$_2$H$_5$)$_3$ |
| Cl$^-$ | (C$_2$H$_5$)$_3$$^+$N—C$_3$H$_6$—Si(OC$_2$H$_5$)$_3$ |
| I$^-$ | (C$_2$H$_5$)$_3$$^+$N—C$_3$H$_4$—Si(OC$_2$H$_5$)$_3$ |
| I$^-$ | (C$_2$H$_5$)$_3$$^+$N—C$_3$H$_6$—Si(OC$_2$H$_5$)$_3$ |
| Cl$^-$ | (C$_4$H$_9$)$_3$$^+$N—C$_3$H$_6$—Si(OC$_2$H$_5$)$_3$ |
| Br$^-$ | (C$_4$H$_9$)$_3$$^+$N—C$_3$H$_6$—Si(OC$_2$H$_5$)$_3$ |

A mixture of two or more of the above-described silanes can be used for the surface modification.

The invention also provides a process for the production of the surface-modified, pyrogenically produced titanium dioxide, which is characterised in that the pyrogenically produced titanium dioxide, in a mixing unit with intensive mixing, optionally in the presence of water or dilute acid, is sprayed with the at least one ammonium-functional silane, or with a solution of the at least one ammonium-functional silane in ethanol, and then further stirred for approximately 10 to 30 minutes and subsequently tempered for between 0.5 and 6 hours at a temperature of 100 to 400° C. The tempering can be carried out in an atmosphere of protective gas, for example, N$_2$.

The pyrogenically produced titanium dioxide used can be a titanium dioxide of the type described in Ullmanns Enzyklopädie der technischen Chemie, 4th Edition, Volume 21 (1982) pages 464–465.

The surface-modified, pyrogenically produced titanium dioxide according to the invention can be used in the field of cosmetics, in particular as a sunblock, also in toner powders, paints and varnishes, in silicone rubber, as abrasives and polishes, for example, in the field of CMP.

In the field of cosmetics, in particular in sunblock preparations, the surface-modified pyrogenically produced titanium dioxide according to the invention exhibits the following IV advantages:

improved absorption of radiation in the range of 300–500 nm good dispersibility in oleophilic and hydrophilic preparations.

EXAMPLES

The titanium dioxide used was the pyrogenically produced titanium dioxide P 25. Titanium dioxide P 25 is known from the series of publications Pigmente No. 56 "Hochdisperse Metalloxide nach dem Aerosilverfahren", 4th Edition, February 1989, Degussa AG.

The physicochemical data for titanium dioxide P 25 is as follows:

|  | Titanium dioxide P 25 |
| --- | --- |
| CAS Reg. Number | 13463-67-7 |
| Behaviour towards water | hydrophilic |
| Appearance | loose white powder |
| BET surface area[1] | 50 ± 15 m$^2$/g |
| Average size of primary particles | 21 nm |
| Tamped density[2] | ca. 100 g/ml |
| Specific weight[10] | ca. 3.7 g/ml |
| Loss on drying[3] on leaving the supplier's premises (2 hours at 105° C.) | <1.5 wt. % |
| Loss on ignition[4][7] (2 hours at 1000° C.) | <2 wt. % |
| pH value[5] (in 4% aqueous dispersion) | 3–4 wt. % |
| $SiO_2$[8] | <0.2 wt. % |
| $Al_2O_3$[8] | <0.3 wt. % |
| $Fe_2O_3$[8] | <0.01 wt. % |
| $TiO_2$[8] | >99.5 wt. % |
| $ZrO_2$[8] | |
| $HfO_2$[8] | |
| $HCl$[8][9] | <0.3 wt. % |
| Screen oversize[6] (after Mocker, 45 µm) | <0.05 wt. % |

[1] in accordance with DIN 66131
[2] in accordance with DIN ISO 787/XI, JIS K 5101/18 (not screened)
[3] in accordance with DIN ISO 787/II, ASTM D 280, JIS K 5101/21
[4] in accordance with DIN 55921, ASTM D 1208, JIS K 5101/23
[5] in accordance with DIN ISO 787/IX; ASTM D 1208, JIS K 5101/24
[6] in accordance with DIN ISO 787/XVIII; JIS K 5101/20
[7] based on the substance dried for 2 hours at 105° C.
[8] based on the substance calcined for 2 hours at 1000° C.
[9] HCl content is a constituent of the loss on ignition
[10] determined by means of a pycnometer with reference to air Preparation - general procedure In the Examples below, $TiO_2$ P25 is placed in a mixer and sprayed with the silane, dissolved in ethanol, with mixing. On conclusion of the spraying, mixing is continued for a further 10 to 30 minutes, followed by tempering for a period of 0.5 to 6 hours at a temperature of 100 to 400° C. The spraying and/or the tempering can be carried out in an atmosphere of protective gas, for example, under nitrogen. Materials and process parameters are described in the table below.

| Example | Silane | Quantity of silane (g/100 g P25) | Quantity of ethanol (g/100 g P25) | Tempering time (h) | Temperature (° C.) |
| --- | --- | --- | --- | --- | --- |
| 1 | Si 270/75 | 5 | 10 | 2 | 120 |
| 2 | Si 270/75 | 7.5 | 0 | 2 | 120 |
| 3 | Si 270/75 | 10 | 20 | 2 | 120 |
| 4 | Si 275/75 | 5 | 10 | 2 | 120 |
| 5 | Si 275/75 | 7.5 | 0 | 2 | 120 |
| 6 | Si 275/75 | 10 | 20 | 2 | 120 |

Silanes used

Si 270/75=Cl$^-$(CH$_3$)$_3$N$^+$—C$_3$H$_6$—Si(OC$_2$H$_5$)$_3$ (75% solution in ethanol)

Si 275/75=Cl$^-$(C$_{18}$H$_{37}$)(CH$_3$)$_2$N$^+$—C$_3$H$_6$—Si(OC$_2$H$_5$)$_3$ (75% solution in ethanol)

Physicochemical data are described in the table below.

1. Physicochemical data

| Example | Silane | Tamped density (g/l) | Carbon content (wt. %) | pH value | Loss on drying (wt. %) | Loss on ignition (wt. %) | CH$_3$OH wettability wt. % |
| --- | --- | --- | --- | --- | --- | --- | --- |
| 1 | Si 270/75 | 225 | 1.3 | 3.7 | 0.5 | 2.9 | 0% |
| 2 | Si 270/75 | 282 | 1.6 | 3.5 | 0.8 | 3.6 | 0% |
| 3 | Si 270/75 | 397 | 2.1 | 3.6 | 0.4 | 4.6 | 0% |
| 4 | Si 275/75 | 215 | 2.1 | 3.6 | 0.8 | 3.4 | 0% |
| 5 | Si 275/75 | 368 | 3.2 | 3.3 | 1.0 | 4.9 | 20% |
| 6 | Si 275/75 | 384 | 3.5 | 3.3 | 0.8 | 5.2 | 10% |

The products exhibit a hydrophilic and oleophilic character and can be used with advantage in cosmetic preprations.

Results of the tests of applicability

The measured UV/VIS spectra of prepared sunblock pastes exhibited good adsorptions in the UV-A and UV-B region.

FIG. 1 compares UV transmission as a function of wavelength of surface-modified, pyrogenically produced titanium dioxide treated with an ammonium-functional silane of the above-described Examples 2 and 5 with a known product T 805. The product T 805 is a pyrogenically produced titanium dioxide which has been treated with a trialkoxyoctylsilane.

These results show that the titanium dioxides according to the invention can be used very effectively in sunblock preparations.

Thus a better absorption of the radiation is achieved primarily in the 300 to 500 nm range.

Obviously, numerous modifications and variations of the present invention are possible in light of the above teachings. It is therefore to be understood that within the scope of the appended claims, the invention may be practiced otherwise than as specifically described herein.

The disclosure of German priority application No. 19929845.9 filed Jun. 29, 1999, is hereby incorporated by reference.

What is claimed is:

1. A product obtained by treating surface-modified, pyrogenically produced titanium dioxide with at least one ammonium-functional silane.

2. The product according to claim 1, and having the following physicochemical data:

| | |
|---|---|
| BET surface area: | 15 to 100 m$^2$/g |
| Bulk density: | 150 to 700 g/l |
| pH value: | 2.5 to 8.5 |
| Loss on drying: | 0.1 to 2.0 wt. % |
| Loss on ignition: | 0.3 to 13.0 wt. % |
| Carbon content: | 0.3 to 12.0 wt. % |
| Methanol wettability: | 0 to 50 wt. %. |

3. The product according to claim 1, wherein the ammonium-functional silane either has the formula:

wherein n=0–3; m=1–3 with n+m<4; y=1–5; X=F, Cl, Br, or I; R=alkyl (C1–C5); R$^1$=alkyl (C1–C18), aryl; R$^2$ and R$^3$ independently=H, alkyl, aryl, or benzyl; R$^4$=H, alkyl, aryl, or —C$_2$H$_4$NR$^5$$_2$ with R$^5$=alkyl;
or is selected from the group consisting of
(RO)$_3$SiC$_3$H$_6$(N$_4$C$_6$H$_{12}$)$^+$X$^-$; (RO)$_3$SiC$_3$H$_6$(pyridinyl)$^+$X$^-$ and
(RO)$_3$SiC$_3$H$_6$OCH$_2$CH(OH)CH$_2$N$^+$(CH$_3$)$_3$X$^-$;
or is selected from the group consisting of

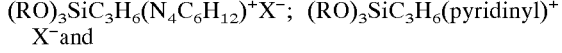

4. The product according to claim 3, wherein the ammonium-functional silane is
X$^-$(CH$_3$)$_3$N$^+$—C$_3$H$_6$—Si(OC$_2$H$_5$)$_3$ or X$^-$(C$_{18}$H$_{37}$)(CH$_3$)$_2$N$^+$—C$_3$H$_6$—Si(OC$_2$H$_5$)$_3$).

5. A process for treating surface-modified, pyrogenically produced titanium dioxide with at least one ammonium-functional silane comprising spraying said at least one silane alone or in an ethanol solution onto said titanium oxide, optionally in the presence of water or dilute acid, while mixing said titanium oxide in a mixing unit, and then further stirring for about 10 to 30 minutes and subsequently tempering for between about 0.5 and 6 hours at a temperature of about 100 to 400° C.

6. The process according to claim 5, wherein the surface-modified, pyrogenically produced titanium dioxide treated with at least one ammonium-functional silane has the following physicochemical data:

| | |
|---|---|
| BET surface area: | 15 to 100 m$^2$/g |
| Bulk density: | 150 to 700 g/l |
| pH value: | 2.5 to 8.5 |
| Loss on drying: | 0.1 to 2.0 wt. % |
| Loss on ignition: | 0.3 to 13.0 wt. % |
| Carbon content: | 0.3 to 12.0 wt. % |
| Methanol wettability: | 0 to 50 wt. %. |

7. The process according to claim 5, wherein the ammonium-functional silane either has the formula:

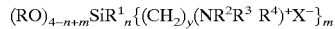

wherein n=0–3; m=1–3 with n+m<4; y=1–5; X=F, Cl, Br, or I; R=alkyl (C1–C5); R$^1$=alkyl (C1–C18), aryl; R$^2$ and R$^3$ independently=H, alkyl, aryl, or benzyl; R$^4$=H, alkyl, aryl, or —C$_2$H$_4$NR$^5$$_2$ with R$^5$=alkyl; or is selected from the group consisting of
(RO)$_3$SiC$_3$H$_6$(N$_4$C$_6$H$_{12}$)$^+$X$^-$, (RO)$_3$SiC$_3$C$_3$H$_6$(pyridinyl)$^+$X$^-$ and
(RO)$_3$SiC$_3$H$_6$OCH$_2$CH(OH)CH$_2$N$^+$(X$^-$,
or is selected from the group consisting of

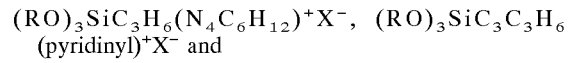

8. The process according to claim 7, wherein the ammonium-functional silane is
X$^-$(CH$_3$)$_3$N$^+$—C$_3$H$_6$—Si(OC$_2$H$_5$)$_3$ or X$^-$(C$_{18}$H$_{37}$)(CH$_3$)$_2$N$^+$—C$_3$H$_6$—Si(OC$_2$H$_5$)$_3$.

9. The process according to claim 8, wherein the ammonium-functional silane is in an ethanol solution.

10. A composition comprising the product according to claim 1, and an additive selected from the group consisting of cosmetic, sunblock, toner powder, paint, varnish, silicone rubber, abrasive and polish additives.

11. The product according to claim 3, wherein the ammonium-functional silane has the formula:

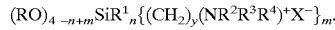

12. The product according to claim 3, wherein the ammonium-functional silane is selected from the group consisting of
(RO)$_3$SiC$_3$H$_6$(N$_4$C$_6$H$_{12}$)$^+$X$^-$, (RO)$_3$SiC$_3$H$_6$(pyridinyl)$^+$X$^-$ and
(RO)$_3$SiC$_3$H$_6$OCH$_2$CH(OH)CH$_2$N$^+$(CH$_3$)$_3$ X$^-$.

13. The product according to claim 3, wherein the ammonium-functional silane is selected from the group consisting of

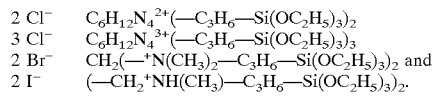

14. The product according to claim 1, wherein the ammonium-functional silane is selected from the group consisting of X$^-$(CH$_3$)$_3$N$^+$—C$_3$H$_6$—Si(OC$_2$H$_5$)$_3$ wherein X=Cl, Br, or I $X^-(C_{18}H_{37})(CH_3)_2N^+$—$C_3H_6$—$Si(OC_2H_5)_3$ wherein X=Cl, Br, or I

| | |
|---|---|
| Cl⁻ | $(CH_3)_3{}^+N$—$C_3H_6$—$Si(OC_2H_5)_3$ |
| I⁻ | $(C_6H_5)(CH_3)_2{}^+N$—$C_3H_6$—$Si(OC_2H_5)_3$ |
| Br⁻ | $(C_6H_5$—$CH_2)(CH_3)_2{}^+N$—$C_3H_6$—$Si(OC_2H_5)_3$ |
| Cl⁻ | $(C_{12}H_{25})(CH_3)_2{}^+N$—$C_3H_6$—$Si(OC_2H_5)_3$ |
| Br⁻ | $(C_{12}H_{25})(CH_3)_2{}^+N$—$C_3H_6$—$Si(OC_2H_5)_3$ |
| I⁻ | $(C_{12}H_{25})(CH_3)_2{}^+N$—$C_3H_6$—$Si(OC_2H_5)_3$ |
| Cl⁻ | $(C_{16}H_{33})(CH_3)_2{}^+N$—$C_3H_6$—$Si(OC_2H_5)_3$ |
| Cl⁻ | $(C_2H_5)_3{}^+N$—$C_3H_6$—$Si(OC_2H_5)_3$ |
| I⁻ | $(C_2H_5)_3{}^+N$—$C_2H_4$—$Si(OC_2H_5)_3$ |
| I⁻ | $(C_2H_5)_3{}^+N$—$C_3H_6$—$Si(OC_2H_5)_3$ |
| Cl⁻ | $(C_4H_9)_3{}^+N$—$C_3H_6$—$Si(OC_2H_5)_3$ |
| Br⁻ | $(C_4H_9)_3{}^+N$—$C_3H_6$—$Si(OC_2H_5)_3$, | and mixtures thereof.

15. A product obtained by treating surface-modified, pyrogenically produced titanium dioxide with at least one ammonium-functional silane, said treating comprising spraying said at least one silane alone or in an ethanol solution onto said titanium oxide, optionally in the presence of water or dilute acid, while mixing said titanium oxide in a mixing unit, and then further stirring for about 10 to 30 minutes and subsequently tempering for between about 0.5 and 6 hours at a temperature of about 100 to 400° C.

16. The product according to claim 15, and having the following physicochemical data:

BET surface area:
15 to 100 m²/g

Bulk density:
150 to 700 g/l pH value:
5 to 8.5

Loss on drying:
1 to 2.0 wt. %

Loss on ignition:
3 to 13.0 wt. %

Carbon content:
3 to 12.0 wt. %

Methanol wettability:
0 to 50 wt. %.

17. The product according to claim 15, wherein the ammonium-functional silane either has the formula:

$(RO)_{4-n+m}SiR^1{}_n\{(CH_2)_y(NR^2R^3R^4)^+X^-\}_m$ wherein n=0–3; m=1–3 with n+m<4; y=1–5; X=F, Cl, Br, or I; R=alkyl (C1–C5); R¹=alkyl (C1–C18), aryl; R² and R³ independently=H, alkyl, aryl, or benzyl; R⁴=H, alkyl, aryl, or —$C_2H_4NR^5{}_2$ with R⁵=alkyl;

or is selected from the group consisting of $(RO)_3SiC_3H_6(N_4C_6H_{12})^+X^-$, $(RO)_3SiC_3H_6(pyridinyl)^+$ X⁻ and $(RO)_3SiC_3H_6OCH_2CH(OH)CH_2N^+(CH_3)_3$ X⁻, or is selected from the group consisting of

| | |
|---|---|
| 2 Cl⁻ | $C_6H_{12}N_4{}^{2+}$(—$C_3H_6$—$Si(OC_2H_5)_3)_2$ |
| 3 Cl⁻ | $C_6H_{12}N_4{}^{3+}$(—$C_3H_6$—$Si(OC_2H_5)_3)_3$ |
| 2 Br⁻ | $CH_2$(—$^+N(CH_3)_2$—$C_3H_6$—$Si(OC_2H_5)_3)_2$ and |
| 2 I⁻ | (—$CH_2{}^+NH(CH_3)$—$C_3H_6$—$Si(OC_2H_5)_3)_2$. |

18. The product according to claim 17, wherein the ammonium-functional silane is $X^-(CH_3)_3N^+$—$C_3H_6$—$Si(OC_2H_5)_3$ or $X^-(C_{18}H_{37})(CH_3)_2N^+$—$C_3H_6$—$Si(OC_2H_5)_3$.

19. The product according to claim 17, wherein the ammonium-functional silane has the formula:

$(RO)_{4-n+m}SiR^1{}_n\{(CH_2)_y(NR^2R^3R^4)^+X^-\}_m$.

20. The product according to claim 17, wherein the ammonium-functional silane is selected from the group consisting of $(RO)_3SiC_3H_6(N_4C_6H_{12})^+X^-$, $(RO)_3SiC_3H_6(pyridinyl)^+$ X⁻ and $(RO)_3SiC_3H_6OCH_2CH(OH)CH_2N^+(CH_3)_3$ X⁻.

21. The product according to claim 17, wherein the ammonium-functional silane is selected from the group consisting of

| | |
|---|---|
| 2 Cl⁻ | $C_6H_{12}N_4{}^{2+}$(—$C_3H_6$—$Si(OC_2H_5)_3)_2$ |
| 3 Cl⁻ | $C_6H_{12}N_4{}^{3+}$(—$C_3H_6$—$Si(OC_2H_5)_3)_3$ |
| 2 Br⁻ | $CH_2$(—$^+N(CH_3)_2$—$C_3H_6$—$Si(OC_2H_5)_3)_2$ and |
| 2 I⁻ | (—$CH_2{}^+NH(CH_3)$—$C_3H_6$—$Si(OC_2H_5)_3)_2$. |

22. The product according to claim 15, wherein the ammonium-functional silane is selected from the group consisting of $X^-(CH_3)_3N^+$—$C_3H_6$—$Si(OC_2H_5)_3$ wherein X=Cl, Br, or I $X^-(C_{18}H_{37})(CH_3)_2N^+$—$C_3H_6$—$Si(OC_2H_5)_3$ wherein X=Cl, Br, or I

| | |
|---|---|
| Cl⁻ | $(CH_3)_3{}^+N$—$C_3H_6$—$Si(OC_2H_5)_3$ |
| I⁻ | $(C_6H_5)(CH_3)_2{}^+N$—$C_3H_6$—$Si(OC_2H_5)_3$ |
| Br⁻ | $(C_6H_5$—$CH_2)(CH_3)_2{}^+N$—$C_3H_6$—$Si(OC_2H_5)_3$ |
| Cl⁻ | $(C_{12}H_{25})(CH_3)_2{}^+N$—$C_3H_6$—$Si(OC_2H_5)_3$ |
| Br⁻ | $(C_{12}H_{25})(CH_3)_2{}^+N$—$C_3H_6$—$Si(OC_2H_5)_3$ |
| I⁻ | $(C_{12}H_{25})(CH_3)_2{}^+N$—$C_3H_6$—$Si(OC_2H_5)_3$ |
| Cl⁻ | $(C_{16}H_{33})(CH_3)_2{}^+N$—$C_3H_6$—$Si(OC_2H_5)_3$ |
| Cl⁻ | $(C_2H_5)_3{}^+N$—$C_3H_6$—$Si(OC_2H_5)_3$ |
| I⁻ | $(C_2H_5)_3{}^+N$—$C_2H_4$—$Si(OC_2H_5)_3$ |
| I⁻ | $(C_2H_5)_3{}^+N$—$C_3H_6$—$Si(OC_2H_5)_3$ |
| Cl⁻ | $(C_4H_9)_3{}^+N$—$C_3H_6$—$Si(OC_2H_5)_3$ |
| Br⁻ | $(C_4H_9)_3{}^+N$—$C_3H_6$—$Si(OC_2H_5)_3$. | and mixtures thereof.

* * * * *